US005743914A

United States Patent [19]

Skiba

[11] Patent Number: 5,743,914
[45] Date of Patent: Apr. 28, 1998

[54] BONE SCREW

[76] Inventor: Jeffry B. Skiba, 4614 E. Thistle Landing Dr., Phoenix, Ariz. 85044

[21] Appl. No.: 659,782

[22] Filed: Jun. 6, 1996

[51] Int. Cl.$^6$ ............................................. A61B 17/86
[52] U.S. Cl. ..................... 606/73; 606/60; 411/412
[58] Field of Search ................... 606/72, 73, 65, 606/66; 411/412, 413

[56] References Cited

U.S. PATENT DOCUMENTS

| Re. 34,969 | 6/1995 | Dixon et al. | 411/412 |
|---|---|---|---|
| 1,809,758 | 6/1931 | Rosenberg | 411/413 |
| 2,263,137 | 11/1941 | Oestereicher | 411/413 |
| 3,207,023 | 9/1965 | Knohl | 411/387 |
| 4,655,661 | 4/1987 | Brandt | 411/387 |
| 5,098,435 | 3/1992 | Stednitz et al. | 606/73 |
| 5,294,227 | 3/1994 | Forster et al. | 411/386 |
| 5,562,672 | 10/1996 | Huebner et al. | 606/73 |

*Primary Examiner*—Michael Buiz
*Assistant Examiner*—David O. Reip

[57] ABSTRACT

A bone screw having a head with a socket for receiving a screw driving device and a shaft extending from the head. The shaft includes respective alternating first and second helical threads running substantially parallel with each other along the shaft. Additionally, the second series of helical threads exhibits a diameter substantially different than the first series of helical threads. In accordance with this aspect of the invention, the thread pattern of the bone screw exhibits a hi-low thread configuration. In addition, the bone screw may comprise a plurality of series of helical threads, each exhibiting different diameters from the others.

17 Claims, 2 Drawing Sheets

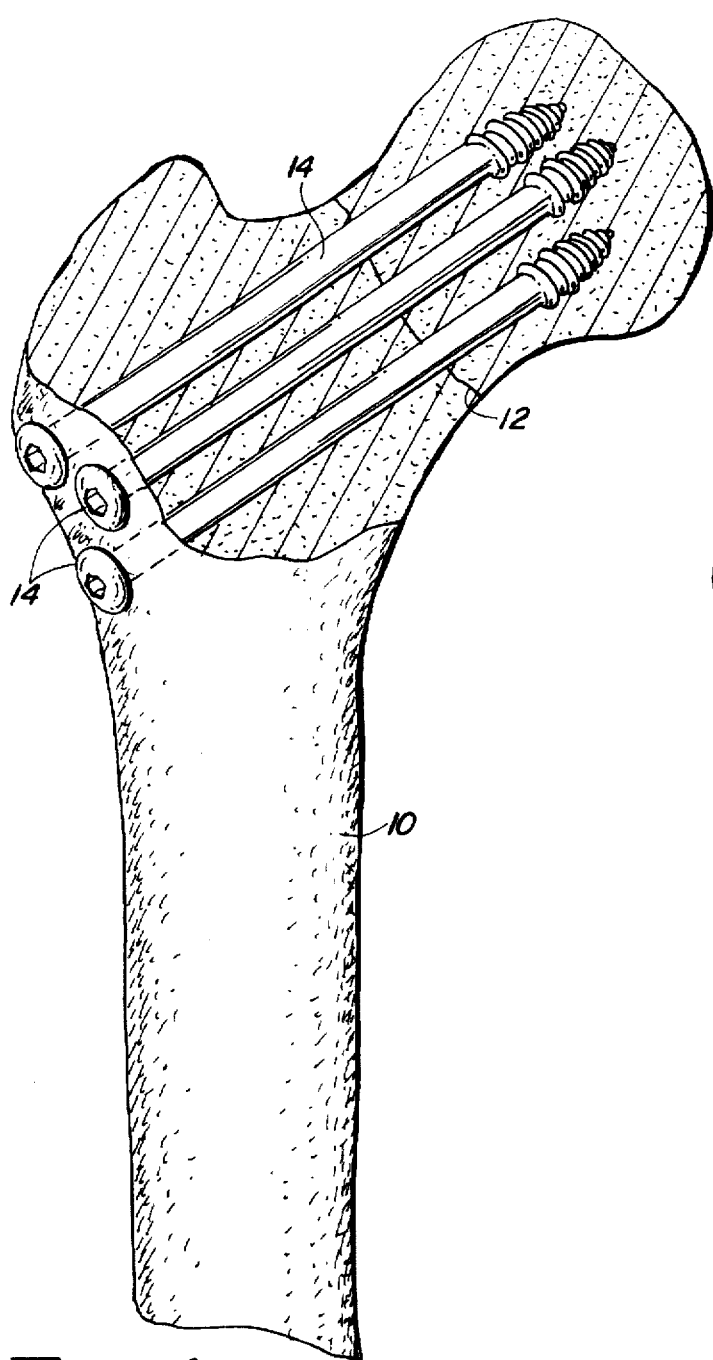
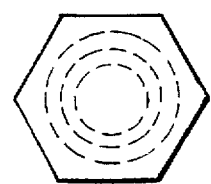
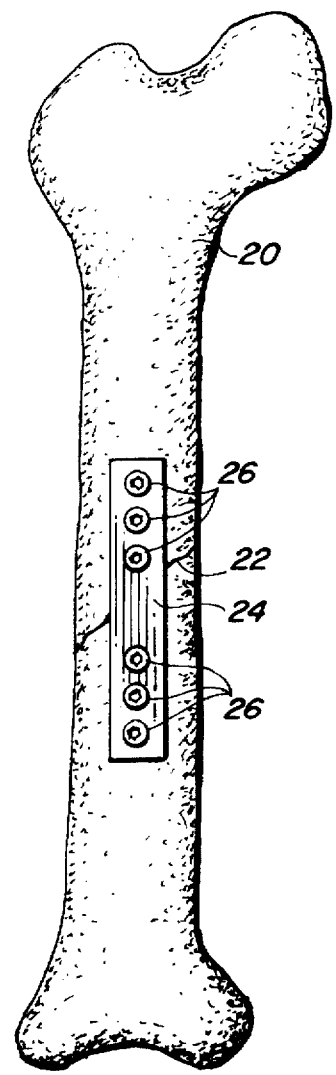
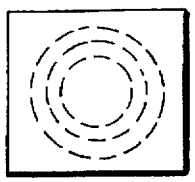

BONE SCREW

TECHNICAL FIELD

This invention generally relates to methods and apparatus for fastening fractured bones and for attaching support plates and/or other prosthetic devices to bone tissue. More particularly, this invention relates to a surgical bone screw having a HI-LO thread configuration for increasing the pullout strength of the screw.

BACKGROUND OF THE INVENTION

It is quite common for human and other animals to fracture bones in their bodies. In some instances, a doctor or orthopedic surgeon can set the fractured bone back into place and it will heal by itself. However, in many instances, fastening devices are used to join the fractured bone to aid the healing process. Bones screws and/or plates are customarily used to reduce the fracture and to maintain the bone pieces in proper physiological alignment during the subsequent healing process. By aligning and compressing the bone pieces together, the capillaries in the bone pieces will bridge together faster, thus decreasing the healing time by as much as three to four weeks.

Bone fastening devices are generally known in the art. In particular, Lorenzo, U.S. Pat. No. 2,242,003 discloses a bone fastening device comprising a lag screw having a head, a shaft and a thread portion. Lorenzo further discloses the use of this fastening device for the reduction and immobilization of a fracture of the neck portion of a femur.

Dezus U.S. Pat. No. 2,489,870 discloses a bone fastening device comprising a lag screw having a threaded end portion, a stud which screws onto the threaded portion and a retaining clip which fastens to the stud so that the stud/clip combination acts as a compression device holding pieces of bone or bone fragments together. This fastening device is particularly useful when the thickness of the material to be fastened cannot be accurately determined in advance, or when the surface of the bone is irregular or uneven.

Hall U.S. Pat. No. 4,041,939 discloses a spinal screw for use in securing a metal cable to a vertebrae to correct scoliosis.

Edwards U.S. Pat. No. 4,569,338 discloses a sacral fixation device comprising a self taping cancellous screw for insertion into the sacrum, the device is configured to accommodate a sacral rod and hook to facilitate longitudinal adjustment of the sacroiliac joint.

Fisher et al. U.S. Pat. No. 4,711,232 discloses a bone fastener including a surgical screw and sleeve. The surgical bone screw disclosed in the Fisher et al. patent is representative of bone screws widely employed in reducing fracture of small bones such as the metacarpals and metatarsals.

Brumfield U.S. Pat. No. 4,827,917 discloses a femoral fracture device including a screw and an intramedullary rod. The screw used in this device is generally a lag type screw.

Finally, Zang U.S. Pat. No. 5,336,225 issued to Zang discloses a surgical bone screw having an asymmetrical head configured to protrude above the surface of the bone.

All of the bone screws disclosed in the prior art generally utilize standard helical thread configurations. However, often times the standard helical thread pattern does not provide sufficient pullout strength or requires high insertion torques which may overstress the bone. Generally, the bone screws used to mend bones and attach prosthetic devices are driven into and must grab and hold the softer cancellous bone tissue typically located in the inner portion of the bone. For many applications, for example in the context of individuals who may not have strong, healthy bones (e.g., smokers and elderly women), currently known bone fastening devices do not provide adequate pullout strength.

A bone screw is thus needed which overcomes the shortcomings of the prior art.

SUMMARY OF THE INVENTION

A surgical bone screw device according to the present invention addresses many of the shortcomings of the prior art.

In accordance with one aspect of the present invention, a bone screw comprises a head with a socket for receiving a screw driving device and a shaft extending from the head. The shaft generally includes respective alternating first and second helical threads running substantially parallel with each other along the shaft (i.e., not intersecting). Additionally, in accordance with the present invention, the second series of helical threads advantageously exhibit a diameter substantially different than the diameter of the first series of helical threads.

In accordance with an alternative embodiment of the present invention, the bone screw may comprise a plurality of series of helical threads, each exhibiting different diameters from the others. In accordance with this embodiment, the plurality of series of threads alternate and run substantially parallel with each other along the screw shaft.

In accordance with yet another aspect of the present invention, a further embodiment of the bone screw may comprise respective first and second series of threads, wherein both series have different diameters and a plurality of the second series of threads are dispersed between the first series of threads.

In accordance with yet another aspect of the present invention, the bone screw may be configured with a variety of different head types and shapes.

In accordance with yet another aspect of the present invention, the bone screw may be configured as a lag screw with the threads extending only part of the way up the shaft, or the screw may be configured with threads extending along the entirety of the shaft.

In accordance with yet another aspect of the present invention, the bone screw may be manufactured from any type of bio-compatible material, for example, titanium alloy, stainless steel, class six implant grade plastic or a material made from bioabsorbables such as polyglycolic acid and the like.

In accordance with yet another aspect of the present invention, the bone screw can exhibit any length, and the diameters of the shaft, the first series of threads and the second series of threads may differ for different types and sizes of the bone in which the screw is to be used.

In accordance with yet another aspect of the present invention, the pitch or threads per inch of the first and second series of threads advantageously differ along the length of the shaft.

In accordance with still another aspect of the present invention, the first series of threads desirably run at a different pitch than the second series of threads and still not intersect.

In accordance with yet another aspect of the present invention, the first series of threads advantageously exhibit a different pitch than the second series of threads, and the first and second series of threads may intersect at one or more points along the shaft of the screw.

In accordance with yet another aspect of the present invention, the hi-lo thread configuration may comprise a single, contiguous thread alternating in height along the shaft of the screw.

These and other aspects the present invention will become more apparent to those skilled in the art from the following non-limiting detailed description of preferred embodiments of the invention taken with reference to the accompanying Figures.

BRIEF DESCRIPTION OF THE DRAWING FIGURES

Preferred exemplary embodiments of the present invention will hereafter be described in conjunction with the appended drawing figures, wherein like designations denote like elements, and:

FIG. 1 is a schematic view of the top portion of a fractured human femur bone with exemplary embodiments of the bone screw of the present invention used to hold the fractured pieces of the femur bone together;

FIG. 2 is a similar schematic view of a fractured human femur bone where bone screws are used to hold a plate to the femur bone to help mend the bone fracture.

FIG. 3A is a top view of another embodiment of the bones screw of FIG. 3 having a square shaped head configuration;

FIG. 3B is a top view of another embodiment of the bone screw of FIG. 3 having a hexagon head configuration;

DETAILED DESCRIPTION OF PREFERRED EXEMPLARY EMBODIMENT

Figure 3:
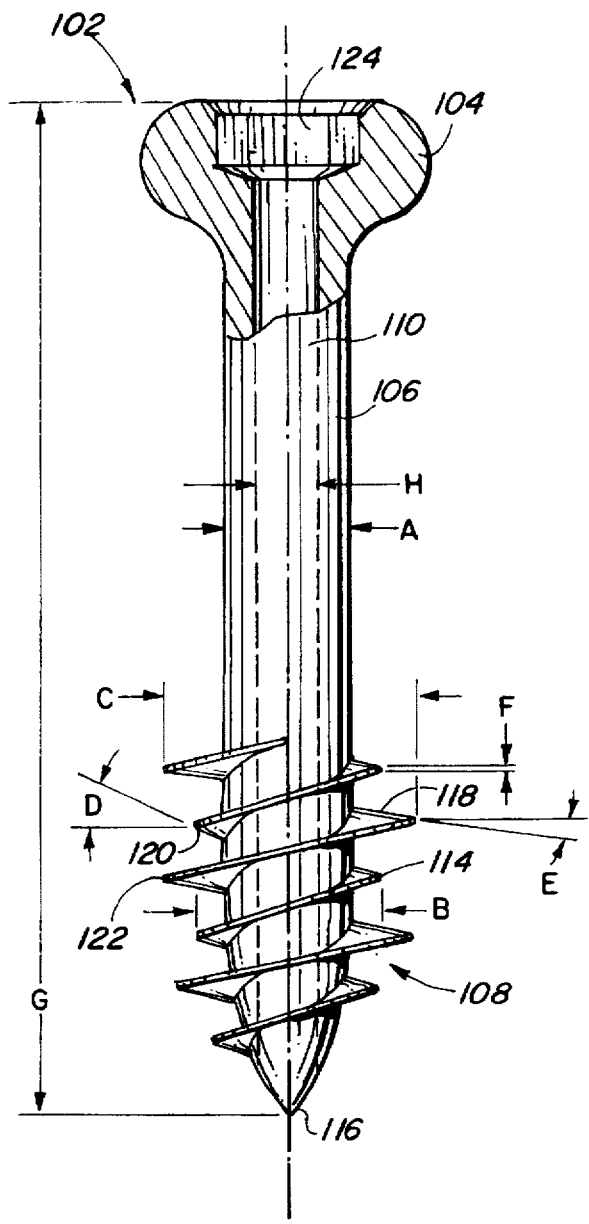
FIG. 3 is a side view of the exemplary embodiment of the bone screw of the present invention showing a cross-sectional view of the head portion of the screw.

As generally known in the medical industry, fractures, especially in larger bones, tend to mend more quickly when the bone is held together with the aid of a fastening device, for example a bone screw or plate. Referring now to FIG. 1, a bone 10, for example, a femur bone of human leg, is shown with a fracture 12 and exemplary bone screws 14 configured to secure the fractured components together to aid the natural mending process.

Similarly, in FIG. 2, a femur bone 20 is shown with a fracture 22 being held together with the aid of a plate 24. To ensure proper compression of the bone, plate 24 is suitably fastened to bone 20 at each side of fracture 22 by bone screws 26, ensuring that fracture 22 is sufficiently compressed together. It should be noted that the bone screws of the present invention can be used for other applications in addition to the mending of bone fractures. For example, in many instances, surgeons will use bone screws as posts for tension band wiring and as suture anchors. Further, the subject bone screws can be used to fasten rods to back bones and install prosthetic devices, as well as many other orthopedic applications. The advantages of the exemplary embodiment in the bone screw described herein applies to all applications of bone fastening devices.

Referring now to FIG. 3, a preferred exemplary embodiment of a bone screw 102 suitably comprises a shaft 106 and a head 104. Shaft 106 is suitably integral with head 104, and in a preferred exemplary embodiment, is substantially cylindrical in shape. Shaft 106 may further include a thread portion 108 towards a distal end or tip 116 of shaft 106 and a substantially smooth middle section between head 104 and thread portion 108, thus exhibiting a lag screw configuration. However, in accordance with a further embodiment of the invention, shaft 106 may exhibit any suitable configuration. For example, shaft 106 may be tapered. That is, the size of the shaft may get larger toward the head of the screw.

In accordance with a preferred exemplary embodiment of the present invention, thread portion 108 of shaft 106 may comprise respective major threads 112 and minor threads 114. In the illustrated embodiment, threads 112 and 114 are each suitably arranged in a helical pattern and run substantially parallel to one another, alternating along shaft 106 of screw 102. In addition, tip 116 of shaft 106 is preferably pointed for easy penetration and self-tapping into the bone matter. Tip 116 may advantageously be formed by tapering or angling of shaft 106, such as at an angle on the order of about 30° to 45°. The outermost point of tip 116 may be sharp, or it may be rounded, such as by being radiused on the order of about 0.010 inch. It should be appreciated, however, that other self-tapping or self-drilling end configurations may be used; for example, tapping flutes or the like. Moreover, alternative pre-tapping end configurations may be employed in the context of shaft 106 and/or that conventional pre-tapping methodologies (e.g. pre-drilling and the like) may be employed as desired even with self-tapping configurations.

A preferred orientation of alternating or interleaved thread patterns 112, 114 is in a so-called "hi-lo configuration". As will be appreciated by those skilled in the art, such a configuration includes minor threads having a diameter of between about 5% to about 99.9%, and more preferably between about 25% to about 75%, and most preferably about 50%, of the diameter of the major threads. Such a configuration with bone screws is believed to offer advantages over other bone screw configurations because it allows for greater recruitment of bone material, and particularly of the soft cancellous bone matter which is typically the part of the boney anatomy to which many screws fasten. Also, the hi-lo thread configuration of the preferred embodiment increases the shear strength of the bone material near the outer edges of the major threads, thus further increasing the pullout strength of the screw. Finally, because only half of the threads have a large diameter, the amount of torque required to drive/set the screw tends to be reduced.

Referring still to FIG. 3, in a preferred exemplary embodiment of the invention, the spacing between either consecutive major threads 112 or of consecutive minor threads 114 is suitably on the order of 5 to 16 threads per inch, and most preferably on the order of about 9 threads per inch. Thus, the spacing of the alternating or interleaved combination of major and minor threads is suitably between about 10 to 32 threads per inch, and most suitably on the order of about 18 threads per inch.

In accordance with a further aspect of a preferred exemplary embodiment, the diameter of shaft 106, as illustrated by dimension A, is suitably on the order of about 0.040 to about 0.200 inch, and more preferably on the order of about 0.060 or 0.190 inch; the diameter of minor threads 114, as illustrated by dimension B measured from the outer edge of one minor thread 114 to the outer edge of another minor thread 114 on the opposite side of shaft 106, is suitably on the order of about 0.060 to about 0.300 inch, and more preferably on the order of about 0.080 to 0.275 inch; and the diameter of major thread 112, as illustrated by dimension C measured from the outer edge of one major thread 112 to the outer edge of another minor thread 112 on the opposite side of shaft 106, is suitably on the order of about 0.075 to about 0.350 inch, and more preferably on the order of about 0.100 to 0.300 inch.

The particular configuration and dimension of threads 112, 114 may vary depending on a variety of factors. For example, the height and number of threads may suitably be chosen to optimize pull-out strength and minimize insertion torque as screw 102 is worked into the bone mass. Preferably, the height of minor thread 114 is between about 25% to about 75% the height of thread 112, and more preferably about 50%.

Figure 4:
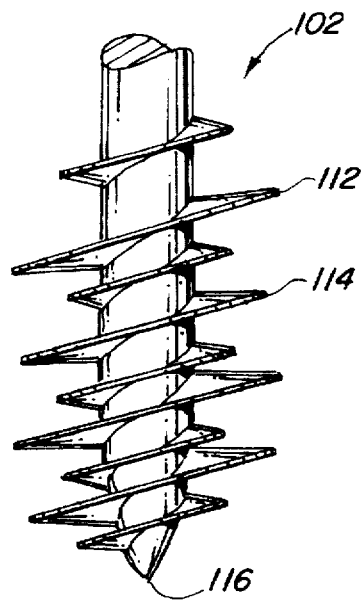
FIG. 4 is a side view of another embodiment of a bone screw wherein the pitch of the first series of helical threads if different than the pitch of the second series of helical threads.
Figure 5:
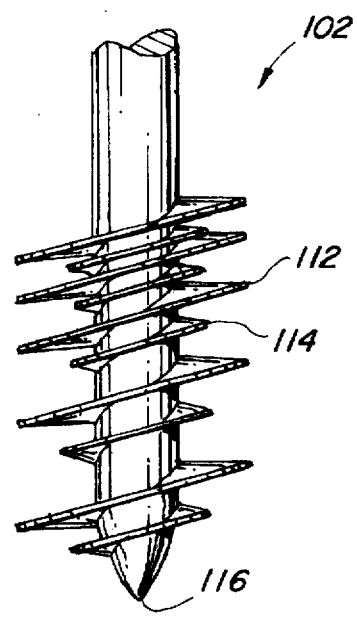
FIG. 5 is a side view of another embodiment of a bone screw wherein the pitches of the first and second series of helical threads change along the length of the shaft of the bone screw.

While screw 102 is shown as having an equal number of major threads 112 and minor threads 114 per inch, it should be appreciated that the number of threads per inch may vary as between the major and minor thread patterns (see FIG. 4), or the thread patterns may vary over the length of screw 102 (see FIG. 5). For example, the number of threads per inch, while typically being the same for both major threads 112 and minor threads 114 might be suitably varied over the length of screw 102, say for example with the pitch increasing from tip 116 to the top or smooth portion of shaft 106 (see FIG. 5). That is, it may be desirable to have more threads per lineal inch in one region along the axis of the shaft than in other regions along the axis of the shaft. It is believed that such a construction may optimize the pull-out strength of screw 102, while at the same time desirably reducing the stress to the bony material upon insertion of screw 102.

It should be noted that the pitch or threads per inch of the major and minor threads may vary independent of each other such that the major thread pattern has a greater or lesser pitch than the minor thread pattern. Depending on the relative pitches and the length of the screw shaft, the screw may be configured with either an intersecting or a non-intersecting thread pattern, as desired.

In yet a further embodiment, the minor thread pattern may have a pitch in the range of 18 threads per inch, while the pitch of the major thread pattern may only be 9 threads per inch. For those embodiments where the first pitch is in the range of two times the second pitch, it may be desirable to employ two substantially parallel thread patterns exhibiting the first pitch interleaved between the second pitch threat pattern.

Threads 112 and 114 may also be suitably surface finished to minimize stress on the bony material as screw 102 is inserted therein. In accordance with a preferred embodiment of this aspect of the present invention, the outer surfaces or edges of threads 112, 114 are optimally rounded or smoothed, for example to exhibit a radiused surface on the order of about 0.002 to about 0.005 inch. As will be appreciated by those skilled in the art, such finish can be engendered through electro-polishing, fine bead sanding or the like.

With continued reference to FIG. 3, in accordance with the illustrated embodiment of the invention, each of respective threads 112 and 114 preferably comprise an angled helical upper surface 118, an angled helical under surface 120, and a helical edge 122 interconnecting surfaces 118 and 120. Preferably, surface 120 is downwardly angled from the outer edge of threads 112 and 114 to the body of shaft 106. This angle is illustrated by dimension D and, in a preferred embodiment, is typically about 10° to 40°, and preferably about 25°. Similarly, upper surface 118 is preferably angled upwardly from the edge of threads 112, 114 to the body of shaft 106, as is illustrated by dimension E, typically about 12° to 10°, and preferably about 5°. The thickness F of the helical edge 122 interconnecting upper surface 118 and lower surface 120 is typically about 0.001 to 0.002 inches, and preferably about 0.005 inch. However, it should be noted that the thickness of helical edge 122 of the major and minor threads may differ. Similarly, the angles of the upper and lower surfaces of the major and minor threads 112, 114 may differ depending on the particular thread configuration.

With continued reference to FIG. 3, head 104 suitably comprises a generally circular cross-sectional shape, and has uniform radii about its entire circumference. Head 104 further comprises a hexagonal-shaped inset 124 which permits insertion of a suitable tool for driving or compressing screw 102 into the bony matter. It should be noted, however, that inset 124 of screw 102 may be any shape sufficient for receiving a driving tool; for example, square, octagonal, etc.

Further, it should be appreciated that other head configurations may be suitably utilized. For example, head 104 may be configured with conventional flat, button, fillister, flat fillister, hex, square or socket heads, or the head may exhibit a head configuration disclosed in Zang U.S. Pat. No. 5,336, 225, the entire disclosure of which is hereby incorporated herein by this reference. Indeed, virtually any head configuration can be utilized in conjunction with the hi-low thread configuration of the present invention. FIGS. 3A and 3B illustrate a square head and a hex head respectively. Moreover, screw 104 may be configured with no head at all. That is, shaft 106 of screw 102 may be configured to receive a driving tool at its end distal from the tip of the screw; for example, shaft 106 may include an inset configured for receiving the driving tool.

Screw 102 may be configured to exhibit any length G depending on the nature and type of bone it is intended to be used with. In accordance with a preferred aspect of the present invention, screw 102 exhibits a length on the order of about 0.25 to 8.0 inches.

In accordance with a further embodiment of the present invention, screw 102 may be suitably configured with an axial bore 110 extending through the entirety thereof, for example, to enable a guide wire to be advantageously passed through screw 102 while in use. In this regard, it may be desirable in some circumstances to insert a guide wire in the exact location that the screw is to be placed to ensure optimal placement of the screw and, thus, proper mending of the bone structure. In this respect, the doctor may install a suitable guide wire into a desired position and slide screw 102 with bore 110 over the wire for screw position guidance. A suitable bore 110 preferably exhibits a diameter H suitably on the order of about 0.020 to about 0.10 inch, and more preferably on the order of about 0.030 to about 0.075 inch. In general, preferably the thickness of the walls of shaft 106 surrounding bore 110 are on the range of about 0.020 to about 0.10, more preferably about 0.025 inch.

In accordance with a further aspect of the present invention, bone screw 102 may be advantageously made from any suitable bio-compatible material, for example titanium alloy, stainless steel, class six implant grade plastic, and the like, or any other bio-compatible material which exhibits adequate pullout strength and having sufficiently low brittleness to avoid breakage during long term usage of the device in situ. Alternatively, in view of the relatively short useful life of device 102 (as discussed above), device 102 may be made from a suitable bio-absorbable material, for example, polylactic, polyoxalic or polyglycolic acids or the like.

In accordance with yet a further aspect of the present invention, screw 102 may be a non-lag screw having threads along the entire length of shaft 106.

In accordance with yet a further aspect of the present invention, a plurality of minor threads 114 may be positioned between each set of major threads 112, or vice versa. Further, the thread configuration may comprise a plurality of threads having different heights. That is, instead of having two sizes of threads (i.e., major and minor threads), screw 102 may have three or more series of threads, all having different thread heights.

In accordance with yet a further aspect of the present invention, the Hi-Lo thread configuration can be used with any type of bone screw including variable length screws, for example, as shown in Asnis U.S. Pat. No. 5,498,265 incorporated herein by reference.

Although the subject invention has been described herein in conjunction with the appended drawing Figures, those skilled in the art will appreciate that the scope of the invention is not so limited. Various modifications in the arrangement of the components discussed and the steps described herein for using the subject device, may be made without departing from the spirit and scope of the invention as set forth in the appended claims.

I claim:

1. A bone screw, comprising:

a head for receiving a screw driving device; and a shaft having a length and extending from said head, said shaft including a first series of helical threads having a first diameter and a first pitch, and a second series of helical threads interleaved with said first series of helical threads and having a second diameter and a second pitch;

wherein said second diameter is substantially different than said first diameter and at least one of said first and second pitches changes along the length of said shaft.

2. The bone screw of claim 1 wherein said head includes a socket for engagement by a driving tool.

3. The bone screw of claim 2 wherein the socket exhibits a hexagon configuration.

4. The bone screw of claim 1 wherein said head is configured as a conventional hexagon head.

5. The bone screw of claim 1 wherein said head is configured as a square shaped head.

6. The bone screw of claim 1 wherein only a portion of said shaft includes said first and said second series of threads.

7. The bone screw of claim 6 wherein a length of the screw is in the range of 0.25 to 8 inches long.

8. The bone screw of claim 1 wherein the shaft further includes a tip distal from the head, the tip being configured for self-tapping the bone screw into the bones.

9. The bone screw of claim 1 wherein the shaft further includes a tip distal from the head, the tip being configured for self-drilling the bone screw into the bones.

10. The bone screw of claim 1 further comprising an axial guide wire bore extending along the length of said screw, such that the guide wire may be journaled through said guide wire bore.

11. The bone screw of claim 1 wherein the first pitch and the second pitch each change along the length of said shaft.

12. The bone screw of claim 1 wherein a diameter of the shaft is in the range of 0.060 to 0.190 inches.

13. The bone screw of claim 12 wherein a diameter of the first series of helical threads is in the range of 0.100 to 0.300 inches.

14. The bone screw of claim 13 wherein a diameter of the second series of helical threads is in the range of 0.080 to 0.275 inches.

15. The bone screw of claim 1 wherein said screw is made of a material selected from the group consisting of titanium alloy, stainless steel, titanium stainless, class six implant grade plastic, polylactic acid, polyoxalic acid, or polyglycolic acid.

16. A bone screw, comprising:

a head for receiving a screw driving device; and a shaft having a length and extending from said head, said shaft including at least two series of interleaved helical threads, each of said series of helical threads having a pitch and having a substantially different diameter than each other of said series of helical threads;

wherein at least one of said series of helical threads changes pitch along the length of said shaft.

17. A bone screw, comprising:

A shaft having a first end, a second end, and a length therebetween, said first end of said shaft being configured to accept a driving device and said second end of said shaft including a first series of helical threads having a first diameter and a first pitch, and at least one second series of helical threads having a second diameter and a second pitch, wherein said second diameter is substantially different than said first diameter and at least one of said first and second pitches changes along the length of said shaft, and wherein said at least one second series of helical threads extend at least part of the way from said first end of said shaft to said second end of said shaft.

* * * * *